US012728147B2

(12) United States Patent
Kim et al.

(10) Patent No.: US 12,728,147 B2
(45) Date of Patent: Sep. 8, 2026

(54) COMPOSITION FOR PREVENTING OR TREATING INFLAMMATORY DISEASE COMPRISING HYDROLYSIS EXTRACT OF PULSATILLA KOREANA AND ANEMONE RADDEANA AS ACTIVE INGREDIENT

(71) Applicant: Ju Youn Back, Seoul (KR)

(72) Inventors: Soong Jin Kim, Goyang-si Gyeonggi-do (KR); Yu Yeon Roh, Seongnam-si Gyeonggi-do (KR)

(73) Assignee: Ju Youn Back, Seoul (KR)

( * ) Notice: Subject to any disclaimer, the term of this patent is extended or adjusted under 35 U.S.C. 154(b) by 643 days.

(21) Appl. No.: 18/000,714

(22) PCT Filed: Jun. 4, 2021

(86) PCT No.: PCT/KR2021/007047

§ 371 (c)(1),
(2) Date: Dec. 5, 2022

(87) PCT Pub. No.: WO2021/246833

PCT Pub. Date: Dec. 9, 2021

(65) Prior Publication Data

US 2023/0210933 A1 Jul. 6, 2023

(30) Foreign Application Priority Data

Jun. 5, 2020 (KR) ........................ 10-2020-0068577

(51) Int. Cl.

*A61K 36/71* (2006.01)
*A61K 45/06* (2006.01)
*A61P 29/00* (2006.01)

(52) U.S. Cl.

CPC .............. *A61K 36/71* (2013.01); *A61K 45/06* (2013.01); *A61P 29/00* (2018.01); *A61K 2236/19* (2013.01); *A61K 2236/333* (2013.01)

(58) Field of Classification Search

None
See application file for complete search history.

(56) References Cited

U.S. PATENT DOCUMENTS

| | | | |
|---|---|---|---|
| 2004/0067263 | A1 | 4/2004 | Liu et al. |
| 2006/0062860 | A1 | 3/2006 | Hu et al. |
| 2008/0268072 | A1 | 10/2008 | Kim et al. |
| 2021/0236576 | A1 | 8/2021 | Ahn et al. |

FOREIGN PATENT DOCUMENTS

| | | | |
|---|---|---|---|
| CN | 103272006 | A | 9/2013 |
| CN | 110559348 | A | 12/2019 |
| KR | 10-0315200 | B1 | 3/2002 |
| KR | 10-2003-0016225 | A | 2/2003 |
| KR | 10-0628334 | B1 | 9/2006 |
| KR | 10-0833216 | B1 | 7/2008 |
| KR | 10-2017-0051918 | A | 5/2017 |
| KR | 10-2018-0005984 | A | 1/2018 |
| KR | 10-2019-0127454 | A | 11/2019 |

OTHER PUBLICATIONS

Zhang Xueping et al., "Anti-inflammatory effect of alcohol extract of Anemone raddeanae on adjuvant arthritis in rats", Pharmacology and Clinics of Chinese Materia Medica, 2016; 32(2): 131-134.

European Search Report issued for European Patent Application No. 21817604.8 on Jun. 21, 2024, 10 pages.

International Search Report issued for International Application No. PCT/KR2021/007047 on Sep. 15, 2021, 6 bages.

Yong Kim et al. "Pulsatilla Saponin D: the Antitumor Principle from Pulsatilla koreana", Arch. Pharm. Res., 2004; 27(9): 915-918.

Bang, S.C., et al. "Triterpenoid saponins from the roots of Pulsatilla koreana", J. Nat. Prod, 2005; 68: 268-272.

Lee S.H., et al. "Anti-inflammatory effects of a methanol extract from Pulsatilla koreana in lipopolysaccharide-exposed ats", BMB Rep., 2012; 45(6): 371-376.

Wei Li, et al. "Anti-Inflammatory and PPAR Transactivational Effects of Oleanane-Type Triterpenoid Saponins from the Roots of Pulsatilla koreana", Biomol Ther., 2014; 22(4): 334-340.

A. Gepdiremen, et al. "Acute anti-inflammatory activity of four saponins isolated from ivy: alpha-hederin, hederasaponin-C, hederacolchiside-E and hederacolchiside-F in carrageenan-induced rat paw edema", Phytomedicine, 2005; 12(6-7): 440-444.

Bang, S.C., et al. "Antitumor activity of Pulsatilla koreana saponins and their structure-activity relationship", Chem. Pharm. Bull. (Tokyo), 2005; 53(11): 1451-1454.

Yong Kim, et al. "Deoxypodophyllotoxin; The Cytotoxic and Antiangiogenic Component from Pulsatilla koreana", Planta Med., 2002; 68(3): 271-274.

Young-Jae You, et al. "Antiangiogenic activity of Bupleurum longiradiatum on human umbilical venous endothelial cells", Archives of Pharmacal Research, 2002; 25(5): 640-642.

You Y.J., et al. "Inhibitory effect of Adonis amurensis components on tube-like formation of human umbilical venous cells", Phytother Res., 2003; 17(5): 568-570.

Nam N.H., et al. "New constituents from Crinum latifolium with inhibitory effects against tube-like formation of human umbilical venous endothelial cells", Nat Prod Res., 2004; 18(6): 485-491.

Chantal Barthomeuf, et al. "Inhibition of HUVEC tubulogenesis by hederacolchiside-A1 is associated with plasma membrane cholesterol sequestration and activation of the Ha-Ras/MEK/ERK cascade", Cancer Chemotherapy and Pharmacology, 2004; 54(5): 432-440.

(Continued)

*Primary Examiner* — Robert A Wax
(74) *Attorney, Agent, or Firm* — ROTHWELL, FIGG, ERNST & MANBECK, P.C.

(57) ABSTRACT

The present invention provides a composition, for preventing or treating an inflammatory disease, comprising, as an active ingredient, a self-hydrolysis extract using a hydrolase in a plant cell from one or more plants selected from *Pulsatilla koreana, Pulsatilla chinensis, Pulsatilla cernua, Anemone raddeana, Aralia elata, Akebia quinata, Lonicera* species, *Adonis amurensis, Hedera helix, Hedera colchica* and *Patrinia scabiosifolia*, and/or additionally an angiogenesis inhibitor.

6 Claims, No Drawings

(56) References Cited

OTHER PUBLICATIONS

Kobayashi S, et al. "Inhibitory effect of isoliquiritin, a compound in licorice root, on angiogenesis in vivo and tube formation in vitro", Biol Pharm Bull, 1995; 18(10): 1382-1386.
Bachran, et al. "Saponins in Tumor Therapy", Mini-Reviews in Medicinal Chemistry, 2008; 8(6): 575-584.
Sun, et al. "Phytochemicals and bioactivities of Anemone raddeana Regel: a review", Pharmazie, 2011; 66(11): 813-821.
Taesook Yoon, et al. "Evaluation of solvent extraction on the anti-inflammatory efficacy of Glycyrrhiza uralensis", Korean Journal of Medicinal Crop Science, 2010; 18(1): 28-33.

COMPOSITION FOR PREVENTING OR TREATING INFLAMMATORY DISEASE COMPRISING HYDROLYSIS EXTRACT OF PULSATILLA KOREANA AND ANEMONE RADDEANA AS ACTIVE INGREDIENT

CROSS REFERENCE TO RELATED APPLICATION

This application is a 35 U.S.C. 371 National Phase Entry Application from PCT/KR2021/007047, filed on Jun. 4, 2021, which claims the benefit of Korean Patent Application No. 10-2020-0068577 filed on Jun. 5, 2020, the disclosures of which are incorporated by reference herein in their entirety.

TECHNICAL FIELD

The present invention relates to a composition containing, as an active ingredient, a hydrolysis extract of *Pulsatilla koreana* and *Anemone raddeana* and/or an angiogenesis inhibitor for preventing or treating an inflammatory disease.

BACKGROUND ART

According to a recent survey of disease burden, aging-related diseases, such as spinal diseases, vascular diseases, chronic degenerative lung diseases, and degenerative arthritis, are on the top of the list of diseases from which the people suffer. Especially, spondyloarthropathy, from which sedentary workers on a computer and the like as well as the elderly frequently suffer, is emerging as a common disease.

Spondyloarthropathy encompasses spinal stenosis, rheumatoid arthritis, lumbar disc disease, cervical disc disease, spinal stenosis, frozen shoulder, degenerative arthritis, and the like, and is mainly caused by degenerative changes in tissues, such as muscles, ligaments, blood vessels, and nerves, around the corresponding spine or joint.

Spinal stenosis is a disease caused by the hypertrophy of ligamentum flavum, which connects vertebrae, due to developmental disorders, birth defects, injuries, and the like. The hypertrophy of ligamentum flavum causes pains by compressing the nerves and muscles around the spine. Immune cells, immune substances, and the like are involved in the hypertrophy of ligamentum flavum, and vigorous angiogenesis also plays an important role in the hypertrophy thereof.

Rheumatoid arthritis is a disease caused by a lesion developed and worsen in the joint synovial membrane due to an immunological response to an antigen that has not yet been well known. Synovial cell proliferation, inflammatory cell infiltration, and active angiogenesis occur in the synovial membrane affected by arthritis, and adhesion molecule formation and various cytokine expression occur on the cell surface. Eventually, the synovial blood vessels are transformed to allow the inflow of white blood cells and the like, which thus form an unusual tissue with other cells and penetrate surrounding tissues. This unusual tissue is called “pannus”. Like in the hypertrophy of ligamentum flavum, vigorous angiogenesis also plays an important role in pannus formation.

Such spondyloarthropathy is associated with inflammation and angiogenesis, and an interest is recently increasing on anti-inflammatory drugs having minimized side effects by isolating compounds exhibiting a strong anti-inflammatory effect from natural plant sources.

An example of bioactive substances that can be obtained from natural plant sources may be saponins. Saponins collectively refer to glycosides widely distributed in the plant kingdom and found in abundance in the families Ranunculaceae, Araliaceae, Dioscoreaceae, Lguminosae, Cucurbitaceae, Compositae, Rosaceae, Liliaceae, Rubiaceae, Rhamnaceae, and Caryophyllaceae.

Saponins contain an aglycone with a steroid, steroid alkaloid, or triterpene scaffold, wherein one or more sugar chains are usually attached to the aglycone (Bachran, C., et al., 2008). Saponins exhibit diversity according to the number of sugar chains attached to the aglycone and the kind of sugar. Saponins having sugars attached to only one functional group of the aglycone are referred to as monodesmosides, and saponins having sugars attached to two functional groups thereof are referred to as bisdesmosides.

Saponins are divided into two types, dammarane-based and oleanane-based saponins, according to the scaffold structure of the aglycone, and most plants contain oleanane-based saponins. The oleanane-based saponins encompass saponins having hederagenin and oleanolic acid as aglycones, and in recent years, oleanane-based saponins, along with the dammarane-based saponins mainly including ginseng saponins, have been known to also have strong biological activity.

For example, *Pulsatilla koreana* containing saponins having an oleanane-based aglycone is a herbal medicine that has been traditionally used for amoebic diseases, killing bacteria, and lumbar pains. According to recent study reports, saponins of *Pulsatilla koreana* show excellent anticancer activity [Y Kim, S C Bang, J H Lee, B Z Ahn. Arch Pharm Res. 2004 September; 27(9):915-8.; Kim Y, Bang S C, Lee J H, Ahn B Z. S C Bang, Y Kim, J H Lee, B Z Ahn. J Nat Prod. 2005 February; 68(2):268-72].

In addition, one recent study has reported that a methanol extract of *Pulsatilla koreana* inhibits the activity of cells and immune substances causing inflammation [S H Lee, E Lee, Y T Ko. BMB reports 45(6):371-6(2012)], and another report has reported that saponins isolated from *Pulsatilla koreana* inhibit the activity of TNF-κB and peroxisome proliferator-activated receptor (PPAR), which are inflammation-inducing substances [W Li, X T Yan, Y N Sun, T T Ngan, S H Shim, Y H Kim. Biomol Ther 22(4), 334-340 (2014)].

Bang et al. isolated 17 kinds of saponins from the roots of *Pulsatilla koreana*, as effective active components of *Pulsatilla koreana*, and analyzed the structures of 6 kinds of saponins thereamong, and as a result, it was confirmed that such saponins have hederagenin, oleanolic acid, betulinic acid, and 23-hydroxybetulinic acid as aglycones and exhibit anticancer and anti-inflammatory activity. The root of *Pulsatilla koreana* also contains deoxypodophyllotoxin (DPT), an angiogenesis inhibitor.

*Anemone raddeana* is a perennial herb belonging to the genus *Anemone* in the family Ranunculaceae and is native to China, Russian Far East, and Korea. It has been known that main active components of *Anemone raddeana* include oleanane triterpenoids and glycosides thereof, which have physiological activity, such as anti-inflammatory activity, anti-tumor activity, pain relief, and anti-convulsant activity (Sun, Y. X., et al., 2011). Especially, the roots of *Anemone raddeana* were confirmed to have 30 kinds of saponins including hederacolchiside A1 (HcolA1) [Y. Zhao, X. Zhan g, Ch. Lu, Y. Yu, Y. Zhan g, J. Lu; J. Food and Drug Analysis; 26(2018), 1113-1121.].

Gepdiremen et al. assessed the anti-inflammatory effect of hederacolchiside E (HcolE), a main component of the root of *Anemone raddeana*, and hederacolchiside F (HcolF), a saponin of *Pulsatilla koreana* on carrageenan-induced rat paw inflammation, and reported that only the effect of HcolF was confirmed in a predetermined range but the effect of HcolE was insignificant [A. Gepdiremen, V Mshvildadze, H Sueleyman, R. Elias. Phytomedicine 12, 440-444(2005)].

In addition, hederacolchiside E (HcolE) and hederacolchiside F (HcolF) are abundant in *Hedera colchica* [M. Getia, V. Mashvildaze, G. Dekanosidze, A. Pichette; Intern. J. Pharmaceutical Sciences and Research 10(2019), 3838-40], and the seeds of *Akebia quinata* also contain saponins with various structures, including HcolF.

Meanwhile, natural extracts may be used as substances that inhibit angiogenesis accompanied by inflammation. For example, *Anthriscus sylbvestris* is a perennial plant that grows well in moist areas at the edge of forests, and deoxypodophyllotoxin (DPT) contained in the roots thereof 100% inhibited HUVEC angiogenesis at a concentration of 3 ng/ml [Y. Kim, S B Song, Y J You, B Z AHN. Planta *Medica.* 68, 271-4(2002)].

*Bupleurum longiradiatum* grows in high and deep mountainous areas across the country, including Jeju island, and contains bupleurotoxin (BPT) and acetylbupleurotoxin (aBPT) as toxic substances. These components 100% inhibited the angiogenesis of human umbilical vein endothelial cells (HUVECs) at a concentration of 30 μg/ml [Y. J. You, I. S. Lee, Y. Kim, K. H. Bae, B. Z. Ahn. Arch. Pharm. Res. 25, 640-2(2002)], and cymarin, cymarol, and cymarilic acid, which are cardenolides contained in the roots of *Adonis amurensis,* 60-80% inhibited the angiogenesis of HUVECs at 1 μg/ml [Y. J. Yoy, Y. Kim, N H Nam, B Z ahn. Phytother. Res. 17, 568-570(2003)].

*Crinum latifolium* (Amarylidaceae) grows in India, Vietnam, and South China, and a solvent extract of the leaves of this plant showed the activity of inhibiting angiogenesis of HUVECs. The action substance was 4-senecioyloxymethyl-3,4-dimethoxycoumarin, and this substance 53% inhibited the angiogenesis of HUVEC at a concentration of 1 μg/ml [N. H. Nam, Y. Kim, Y. J. You, D H Hong, H. M. Kim, B. Z. Ahn. Nat. Prod. Res. 18(6):485-91(2004)].

It has been reported that hederacolchiside A1 (HcolA1) isolated from the roots of *Anemone raddeana* also 100% inhibited the angiogenesis of HUVECs at a concentration of 2 μg/ml. However, it has been reported that hederacolchiside A (HcolA) in which an OH group instead of a hydrogen atom is attached to carbon at position 23 in the structure of hederacolchiside A1 (HcolA1) did not show such activity [C I Barthomerf, D Boivin, R Beliveau. Cancer Chemother. Pharmacol. 54, 432-40(2004)].

*Glycyrrhiza uralensis, Glycyrrhiza glabra*, and the like belong to the genus *Glycyrrhiza*, and the roots thereof are commonly used as a medicine to protect the spleen and harmonize the detoxification and drug actions in oriental medicine. *Glycyrrhiza uralensis* has pharmacological actions, such as detoxicating action, anti-inflammatory action, and anti-ulcer action, against pathogenic poisoning, food poisoning, and the like. *Glycyrrhiza uralensis* contains, as main components, saponins, such as glycyrrhizin, and also contain flavone components, such as liquiritin and isoliquiritin. In 1995, Kobayashi et al. discovered that a water extract of *Glycyrrhiza uralensis* inhibited granuloma angiogenesis and confirmed a corresponding active ingredient to be isoliquiritin (Kobayashi S et al., 1995).

The present inventors, through prior research, received a patent on a method for preparing a *Pulsatilla koreana* composition by converting 3-O—[O-α-L-rhamnopyranosyl-(1→2)-[O-β-D-glucopyranosyl-(1→4)]-α-L-arabinopyranosyl] hederagenin 28-O-α-L-rhamnopyranosyl-(1→4)-O-β-D-glucopyranosyl-(1→6)-p-D-glucopyranosyl ester, as a saponin of *Pulsatilla koreana*, into 3-O—[O-α-L-rhamnopyranosyl-(1→2)-[O-β-D-glucopyranosyl-(1→4)]-α-L-arabinopyranosyl] hederagenin, as a saponin of *Pulsatilla koreana* having a strong anticancer effect, through hydrolysis using enzymes retained in *Pulsatilla koreana* itself and then conducting extraction (Korean Patent NO. 628334).

However, the efficiency of hydrolysis of the *Pulsatilla koreana* extract through the enzymes of *Pulsatilla koreana* itself was low, and an anti-inflammatory composition using hydrolysis extracts of *Pulsatilla koreana* and *Anemone raddeana* is not disclosed.

Accordingly, while researching methods capable of maximizing the anti-inflammatory ability of oleanane-based saponins isolated from various plants including *Pulsatilla koreana* and the anti-inflammatory effect of the compounds, the present inventors established an anti-inflammatory composition having excellent anti-inflammatory activity and using *Pulsatilla koreana* and *Anemone raddeana* roots and an angiogenesis inhibitory extract and a preparation method therefor, and thus completed the present invention.

The prior art Korean Patent Application Publication No. 2003-16225 discloses a medicament useful for treating aseptic inflammations, containing an extract of *Pulsatilla koreana* and an extract of *Anemone raddeana*, but does not disclose an anti-inflammatory composition hydrolysis extracts of *Pulsatilla koreana* and *Anemone raddeana* and/or an angiogenesis inhibitor of the present invention.

Korean Patent Application Publication No. 2018-5984 discloses a composition, containing a *Pulsatilla koreana* extract and an *Adonis amurensis* extract, for preventing and relieving fatigue, but does not disclose hydrolysis extracts and/or an angiogenesis inhibitor of *Pulsatilla koreana* and *Adonis amurensis* and an excellent anti-inflammatory composition containing the same in the present invention.

PRIOR ART DOCUMENTS

Patent Documents

Korean Patent No. 628334, a method of improving anticancer effect of *Pulsatilla koreana* and a composition prepared by the method, 19 Sep. 20006

Korean Patent Publication No. 2003-16225, a medicament useful for treating aseptic inflammations, containing anemonin as an active ingredient, 26 Feb. 2003

Korean Patent Publication No. 2018-5984, a composition for preventing and relieving fatigue, 17 Jan. 2018

Non-Patent Documents

Yong K., Seong-Cheol B., J. H Lee, B. Z Ahn, *Pulsatilla* Saponin D: the Antitumor Principle from *Pulsatilla koreana*. Arch. Pharm. Res. 27(9), 915-918, (2004)

Bang, S. C., Kim, Y., Lee, J. H. Ahn B. Z., Triterpenoid saponins from the roots of *Pulsatilla koreana*. J. Nat. Prod, 68, 268-272, (2005)

Lee S. H., Lee E, Ko Y. T., Anti-inflammatory effects of a methanol extract from *Pulsatilla koreana* in lipopolysaccharide-exposed rats. BMB Rep., 45(6): 371-376, (2012)

Wei Li, Xi Tao Yan, Ya Nan Sun, Thi Thanh Ngan, Sang Hee Shim, Young Ho Kim, Anti-Inflammatory and PPAR Transactivational Effects of Oleanane-Type Triterpenoid Saponins from the Roots of *Pulsatilla koreana*, Biomol Ther., 22(4), 334-340, (2014)

A. Gepdiremen, V Mshvildadze, H Sueleyman, R. Elias., Acute anti-inflammatory activity of four saponins isolated from ivy: alpha-hederin, hederasaponin-C, hederacolchiside-E and hederacolchiside-F in carrageenan-induced rat paw edema, Phytomedicine, 12(6-7), 440-444, (2005)

Bang, S. C., et al., Antitumor activity of *Pulsatilla koreana* saponins and their structure-activity relationship, Chem. Pharm. Bull. (Tokyo), 53(11), 1451-1454, (2005)

Yong Kim, Song-Bae Kim, Young-Jae You, Byung-Zun Ahn, Deoxypodophyllotoxin; The Cytotoxic and Antiangiogenic Component from *Pulsatilla koreana*, Planta Med., 68(3), 271-274, (2002)

Young-Jae You, Im-Seon Lee, Yong Kim, Ki-Hwan Bae, Byung-Zun Ahn, Antiangiogenic activity of *Bupleurum longiradiatum* on human umbilical venous endothelial cells, Archives of Pharmacal Research, 25(5), 640-642, (2002)

You Y. J., Kim Y., Nam N. H., Ahn B. Z., Inhibitory effect of *Adonis amurensis* components on tube-like formation of human umbilical venous cells, Phytother Res. 17(5), 568-570, (2003)

Nam N. H., Kim Y., You Y. J., Hong D. H., Kim H. M., Ahn B. Z., New constituents from *Crinum latifolium* with inhibitory effects against tube-like formation of human umbilical venous endothelial cells, Nat Prod Res. 18(6), 485-491, (2004 December)

Chantal Barthomeuf, Dominique Boivin, Richard Bliveau, Inhibition of HUVEC tubulogenesis by hederacolchiside-A1 is associated with plasma membrane cholesterol sequestration and activation of the Ha-Ras/MEK/ERK cascade, Cancer Chemotherapy and Pharmacology, 54(5), 432-440, (2004)

Kobayashi S, Miyamoto T, Kimura I, Kimura M., Inhibitory effect of isoliquiritin, a compound in licorice root, on angiogenesis in vivo and tube formation in vitro. Biol Pharm Bull, 18(10), 1382-6, (1995 October)

DISCLOSURE OF INVENTION

Technical Problem

An aspect of the present invention is to provide an anti-inflammatory composition containing a hydrolysis extract of *Pulsatilla koreana* and *Anemone raddeana* roots.

An aspect of the present invention is to provide an anti-inflammatory composition containing an angiogenesis inhibitor in addition to a hydrolysis extract of *Pulsatilla koreana* and *Anemone raddeana* roots.

An aspect of the present invention is to develop an anti-inflammatory composition containing saponins and having excellent anti-inflammatory activity on spondyloarthropathy by increasing the contents of active saponins through cross hydrolysis of *Pulsatilla koreana* and *Anemone raddeana* root extracts and by additionally containing an angiogenesis inhibitor and to develop a novel natural product drug, composed of the anti-inflammatory composition, for treating spondyloarthropathy.

Solution to Problem

The present invention provides a hydrolysis extract of *Pulsatilla koreana* and *Anemone raddeana* roots and an anti-inflammatory composition containing the same.

HcolF and HcolE contained in *Pulsatilla koreana* or *Anemone raddeana* roots are saponins having hederagenin or oleanolic acid as an aglycone, and are mainly present as a bisdesmoside (ester), which is a storage form in plant cells. However, the substances exhibit a high anti-inflammatory effect when being in a state of a monodesmoside (free carboxylic acid), which is a hydrolysate thereof, but present in the form of a bisdesmoside (ester) in the natural state.

In the present invention, the term hydrolysis extract refers to an extract of a compound in a lower molecular weight unit, separated from a compound in a storage form in plant cells by using an enzyme, a coenzyme, or the like derived from inside or outside the plant, and hereinafter, the term fermentation product or fermentation extract are also used in the same sense.

The present inventors established a method for preparing an extract containing high contents of anti-inflammatory saponins by converting the saponin bisdesmoside (ester) contained in *Pulsatilla koreana* or *Anemone raddeana* roots to the saponin monodesmoside having high anti-inflammatory activity and confirmed anti-inflammatory activity of the extract, and confirmed that the composition, when further mixed with a mixture of the composition with an extract of at least one selected from the group consisting of *Anthriscus sylvestris, Bupleurum longiradiatum, Adonis amurenis, Crinum latifolium*, and *Glycyrrhiza uralensis*, which contain an angiogenesis inhibitor, or an angiogenesis inhibitor (deoxypodophyllotoxin or the like) isolated therefrom, showed a significantly enhanced anti-inflammatory effect, and then completed the present invention.

In addition, extracts containing high-concentrations of saponins having hederagenin and oleanolic acid as aglycones are mixed with an angiogenesis inhibitory plant extract, thereby increasing an anti-inflammatory effect.

Examples of the plants containing large amounts of saponins having hederagenin and oleanolic acid as aglycones is *Pulsatilla koreana*, anemone plants (*Anemone raddeana, Adonis amurensis*, etc.), ivy plants (*Hedera helix, Hedera colchica*, etc.), *Akebia quinata* seeds, and the like. Specifically, such plants may be plants belonging to the families Ranunculaceae, Araliaceae, Dioscoreaceae, Leguminosae, Cucurbitaceae, Compositae, Rosaceae, Liliaceae, Rubiaceae Rhamnaceae, and Caryophyllaceae.

More specifically, such plants may be at least one selected from the group consisting of *Pulsatilla koreana, Pulsatilla chinensis, Pulsatilla cernua, Anemone raddeana, Aralia elata, Akebia quinata, Lonicera species, Adonis amurensis, Hedera helix, Hedera colchica*, and *Patrinia scabiosifolia.*

An example of the saponins having hederagenin or oleanolic acid as an aglycone may be hederacolchiside A (HcolA) or hederacolchiside A1 (HcolA1). HcolA or HcolA1 may be formed by hydrolysis of hederacolchiside E or hederacolchiside F.

The hydrolysis may be hydrolysis by an enzyme contained in an extract of a plant containing an oleanane-based saponin in abundance. The hydrolysis may be hydrolysis of an extract of a plant containing an oleanane-based saponin in abundance together with an extract of a plant containing an oleanane-based saponin in abundance. As described above, the extract of a plant may be an extract prepared by adding an organic solvent to an extract obtained by extraction of a ground material of the plant with water.

In the prior experiment, a ground material of a plant, obtained by adding a predetermined amount of water to the plant body to grind the plant body, exhibited a macromolecule form in which bisdesmoside saponins are combined with and fused to other substances. Therefore, the present inventors attempted to increase the content of monodesmosides in a plant body by adding a predetermined amount of water to the ground material of the plant and allowing the hydrolysis of macromolecules in the plant body under predetermined conditions.

When two or more species of plants are used to utilize two or more kinds of hydrolases therein, the content of saponins in a monodesmoside form in the two or more species of plants can be significantly increased.

Hereinafter, preferable exemplary embodiments of the present disclosure will be described in detail.

The composition for preventing or treating an inflammatory disease of the present invention may be a composition containing an organic solvent extract of a water-hydrolysis fermentation product of a ground material of at least one plant selected from *Pulsatilla koreana, Pulsatilla chinensis, Pulsatilla cernua, Anemone raddeana, Aralia elata, Akebia quinata, Lonicera species, Adonis amurensis, Hedera helix, Hedera colchica*, and *Patrinia scabiosifolia*.

The organic solvent may be at least one solvent selected from the group consisting of C1 to C4 lower alcohols, acetone, and ethyl acetate. Therefore, the present invention provides a composition for preventing or treating an inflammatory disease, the composition containing an extract obtained by mixing and hydrolyzing a water-hydrolysis fermentation product of a ground material of at least one plant selected from the group consisting of *Pulsatilla koreana* and *Anemone raddeana* and an extract of at least one plant selected from the group consisting of *Pulsatilla koreana* and *Anemone raddeana* with an organic solvent selected from C1 to C4 lower alcohols, acetone, and ethyl acetate.

The inflammatory disease may be at least one selected from the group consisting of spinal stenosis, rheumatoid arthritis, lumbar disc disease, cervical disc disease, spinal stenosis, frozen shoulder, and degenerative arthritis.

The composition for preventing or treating an inflammatory disease may further contain an extract of at least one plant selected from the group consisting of *Anthriscus sylvestris, Bupleurum longiradiatum, Adonis amurenis, Crinum latifolium, Glycyrrhiza uralensis*, and *Glycyrrhiza glabra*, the extract having angiogenesis inhibitory action.

Furthermore, the prevent invention provides a composition for preventing or treating an inflammatory disease, the composition further containing at least one angiogenesis inhibitor selected from the group consisting of deoxypodophyllotoxin (DPT), vinblastine, vincristine, vinorelvine, paclitaxel, docetaxel, camptothecin, topotecan, irinotecan, belotecan, podophyllotoxin, etoposide, teniposide, bupleurotoxin (BPT), acetylbupleurotoxin (aBPT), cymarin, cymarilic acid, cymarol, isoliquiritin, and 4-senecioyloxymethyl-3,4-dimethoxycoumarin.

The present invention provides a composition for preventing or treating an inflammatory disease, the composition containing an extract obtained by mixing and hydrolyzing a water-hydrolysis fermentation product of a ground material of at least one plant selected from the group consisting of *Pulsatilla koreana* and *Anemone raddeana* and an extract of at least one plant selected from the group consisting of *Pulsatilla koreana* and *Anemone raddeana* with an organic solvent selected from C1 to C4 lower alcohols, acetone, and ethyl acetate, wherein the composition further contains at least one angiogenesis inhibitor selected from the group consisting of deoxypodophyllotoxin (DPT), vinblastine, vincristine, vinorelvine, paclitaxel, docetaxel, camptothecin, topotecan, irinotecan, belotecan, podophyllotoxin, etoposide, teniposide, bupleurotoxin (BPT), acetylbupleurotoxin (aBPT), cymarin, cymarilic acid, cymarol, isoliquiritin, and 4-senecioyloxymethyl-3,4-dimethoxycoumarin.

The angiogenesis inhibitor may be preferably at least one selected from the group consisting of deoxypodophyllotoxin (DPT), cymarin, cymarilic acid, isoliquiritin, and cymarol.

The composition for preventing or treating an inflammatory disease may be prepared by a method including:

i) a first step of preparing a first plant extract by adding distilled water to at least one first plant selected from *Pulsatilla koreana, Pulsatilla chinensis, Pulsatilla cernua, Anemone raddeana, Aralia elata, Akebia quinata, Lonicera species, Adonis amurensis, Hedera helix, Hedera colchica*, and *Patrinia scabiosifolia*, followed by grinding;

ii) a second step of preparing a second plant extract by adding an organic solvent to at least one second plant selected from *Pulsatilla koreana, Pulsatilla chinensis, Pulsatilla cernua, Anemone raddeana, Aralia elata, Akebia quinata, Lonicera* species, *Adonis amurensis, Hedera helix, Hedera colchica*, and *Patrinia scabiosifolia;* iii) a third step of mixing the first plant extract in the first step and the second plant extract in the second step, followed by hydrolysis with stirring at 37° C.;

iv) a fourth step of fractionating a hydrolysate obtained through the hydrolysis in the third step by adding an organic solvent thereto;

v) a fifth step of applying a fraction in the fourth step to column chromatography to obtain an eluate; and vi) a sixth step of fractionating the eluate in the fifth step by adding an organic solvent thereto, thereby obtaining a fraction.

As for the "first plant extract", the plant body is a reaction chamber for hydrolysis and used as a substrate for hydrolysis, and during the isolation of saponin glycosides from the plant, an ester group of a saponin is hydrolyzed by a hydrolase present in plant cells.

The first plant for the "first plant extract" may be any plant that has hydrolase in plant cells and contain saponins, and the first plant may be preferably at least one selected from the group consisting of *Pulsatilla koreana, Pulsatilla chinensis, Pulsatilla cernua, Anemone raddeana, Aralia elata, Akebia quinata, Lonicera species, Adonis amurensis, Hedera helix, Hedera colchica*, and *Patrinia scabiosifolia*. The first plant may be more preferably at least one selected from the group consisting of *Pulsatilla koreana, Pulsatilla chinensis, Pulsatilla cernua, Anemone raddeana, Adonis amurensis, Hedera helix*, and *Hedera colchica*, and still more preferably at least one selected from the group consisting of *Pulsatilla koreana* and *Anemone raddeana.*

The first plant extract in the first step may be prepared by the steps of: adding distilled water to the first plant, followed by primary grinding in a blender, and subjecting the primarily ground material to secondary grinding through ultrasonication.

The second plant, which is hydrolyzed in the first plant extract, may be any plant that contains saponins, and the second plant is preferably at least one selected from the group consisting of *Pulsatilla koreana, Pulsatilla chinensis, Pulsatilla cernua, Anemone raddeana, Aralia elata, Akebia quinata, Lonicera species, Adonis amurensis, Hedera helix, Hedera colchica*, and *Patrinia scabiosifolia*. The second plant is more preferably at least one selected from the group consisting of *Pulsatilla koreana, Anemone raddeana, Adonis amurensis, Hedera helix*, and *Hedera colchica*, and still more preferably at least one selected from the group consisting of *Pulsatilla koreana* and *Anemone raddeana.*

The roots, leaves, fruits, seeds, and the like of the plant bodies may be used in the preparation of the first plant extract and the second plant extract. However, the seeds containing plant oils in abundance are not preferable since the removal process of plant oils is complicated, and the leaves containing chlorophylls or waxes are not preferable since hydrolases may be inactivated during the removal of chlorophylls or waxes. Preferably, the roots and flesh of the plant bodies may be used.

The second plant extract in the second step may be an extract obtained by extraction with at least one solvent selected from the group consisting of C1 to C4 lower alcohols, acetone, ethyl acetate, and hexane, wherein the C1 to C4 lower alcohols may be methanol, ethanol, propanol, isopropanol, butanol, and the like.

The plant extract may be a fraction obtained by subjecting a plant to extraction with at least one solvent, selected from the group consisting of C1 to C4 lower alcohols, acetone, ethyl acetate, and hexane, to obtain an extract, concentrating the extract to a concentrate, and then fractionating the concentrate with an organic solvent.

The hydrolysis in the third step is to hydrolyze a glycosyl ester group at position 28 in saponins present in the plant to form a free acidic functional group, thereby converting the saponins to anti-inflammatory saponins having high anti-inflammatory activity. In the hydrolysis, the hydrolase that is present in the medium of the plant itself is used to hydrolyze a glycosyl ester of saponins in the medium of the plant itself and the plant extract, thereby converting the saponins to anti-inflammatory saponins.

The first plant for the first plant extract and the second plant hydrolyzed in the first plant extract may be cross hydrolyzed in each other. *Pulsatilla koreana* for the first plant and *Anemone raddeana* for the second plant are selected, and the second plant extract of *Anemone raddeana* may be hydrolyzed in the first plant extract of *Pulsatilla koreana*. Conversely, *Anemone raddeana* for the first plant and *Pulsatilla koreana* for the second plant are selected, and the second plant extract of *Pulsatilla koreana* may be hydrolyzed in the first plant extract of *Anemone raddeana*. In addition, the first plant for the first plant extract and the second plant hydrolyzed in the first plant extract may be the same species of plant. For example, the second plant extract, which is an organic solvent extract of *Pulsatilla koreana*, may be hydrolyzed in the first plant extract, which is a water extract of *Pulsatilla koreana*. The second plant may be selected according to the mixing ratio of desired saponin types.

The effective anti-inflammatory compound contained in the hydrolysate of *Pulsatilla koreana* is mainly hederacolchiside A, which is obtained by hydrolysis from hederacolchiside F and is a saponin having hederagenin as an aglycone. The effective anti-inflammatory compound contained in the hydrolysate of *Anemone raddeana* roots is hederacolchiside A1, which is obtained by hydrolysis from hederacolchiside E and is a saponin having oleanolic acid as an aglycone.

A cross hydrolysate may be obtained through the cross hydrolysis, and thus the present invention can maximize the content of monodesmosides with excellent anti-inflammatory activity. In addition, an anti-inflammatory natural composition in which the content ratio of hederacolchiside A (HcolA) having hederagenin as an aglycone and hederacolchiside A1 (HcolA1) having oleanolic acid as an aglycone is 1:2 to 2:1 can be provided by controlling the species of the first and second plants and the mixing ratio thereof. The anti-inflammatory activity was best when the content ratio of HcolA and HcolA1 was 1:1, and was degraded when the content ratio of HcolA and HcolA1 exceeded a range of 1:2 to 2:1, for example, 1:3 or 3:1.

In the fourth step, the hydrolysate obtained through hydrolysis is fractionated by addition of an organic solvent.

In the fifth step, the fraction in the fourth step is subjected to column chromatography to secure an eluate. The column chromatography in the fifth step may be selected from silica gel column chromatography, HP-20 column chromatography, RP-18 column chromatography, LH-20 column chromatography, high-performance liquid chromatography, reverse phase HPLC, and the like.

In the sixth step, the fraction may be obtained by adding an organic solvent to the eluate in the fifth step to fractionate the eluate. The organic solvent in the fourth step or the sixth step may include a C1 to C4 lower alcohol, ethyl acetate, hexane, and acetone. The C1 to C4 lower alcohol may be methanol, ethanol, propanol, isopropanol, butanol, or the like, preferably methanol or ethanol, and more preferably methanol.

The anti-inflammatory compositions of the present invention can enhance an anti-inflammatory effect by mixing a plant-derived substance inhibiting angiogenesis with extracts containing high-concentrations of saponins having hederagenin and oleanolic acid as aglycones.

The method may further include, after the sixth step, a seventh step of mixing the fraction in the sixth step with an angiogenesis inhibitor. The angiogenesis inhibitor in the seventh step has been reported to play an important role in the hypertrophy of ligamentum flavum or the inhibition of pannus formation in spondyloarthropathy. The present invention confirmed that the combination of saponins with such angiogenesis inhibitors maximized the synergistic effect in the treatment of spondyloarthropathy.

The angiogenesis inhibitor according to the present invention may be a plant extract, and a plant extract usable as the angiogenesis inhibitor may be an extract of *Anthrascus sylvestris, Bupleurum longiradiatum, Adonis amurensis, Crinum latfolium, Glycyrrhiza uralensis, Glycyrrhiza glabra*, or *Anemone raddeana*. A synergistic effect in the anti-inflammatory action can be obtained by mixing an angiogenesis inhibitory extract obtained from the plants with a saponin-containing extract.

The plant extract may be an extract of a plant belonging to the families Ranunculaceae, Araliaceae, Dioscoreaceae, Leguminosae, Cucurbitaceae, Compositae, Rosaceae, Liliaceae, Rubiaceae, Rhamnaceae, Caryophyllaceae, and the like, but is not limited thereto. The plant extract may be preferably an extract of at least one selected from the group consisting of *Anthriscus sylvestris, Bupleurum longiradiatum, Adonis amurenis, Crinum lanfolium, Glycyrrhiza uralensis*, and *Glycyrrhiza glabra*, and more preferably an *Adonis* amurenis extract or a *Glycyrrhiza uralensis* extract.

The angiogenesis inhibitor may be a compound obtained by purification of an angiogenesis inhibitory plant extract. The compound obtained by purification of an angiogenesis inhibitory plant extract may include vinblastine, vincristine, vinorelvine, paclitaxel, docetaxel, camptothecin, topotecan, irinotecan, belotecan, podophyllotoxin, etoposide, teniposide, deoxypodophyllotoxin (DPT), bupleurotoxin (BPT), acetylbupleurotoxin (aBPT), cymarin, cymarilic acid, cymarol, isoliquiritin, and 4-senecioyloxymethyl-3,4-dimethoxycoumarin, and may be preferably at least one selected from the group consisting of deoxypodophyllotoxin, bupleurotoxin (BPT), acetylbupleurotoxin (aBPT), cymarin, cymarilic acid, cymarol, isoliquiritin, and 4-senecioyloxymethyl-3,4-dimethoxycoumarin, and most preferably, at least one selected from the group consisting of deoxypodophyllotoxin (DPT), cymarin, cymarilic acid, isoliquiritin, and cymarol.

The composition, for preventing or treating an inflammatory disease, containing, as an active ingredient, a hydrolysis extract of *Pulsatilla koreana* and *Anemone raddeana* and/or at least one extract selected from the group consisting of *Anthriscus sylvestris, Bupleurum longiradiatum, Crinum latifolium*, and *Adonis* amurenis, may be a pharmaceutical composition.

The pharmaceutical composition may contain a pharmaceutically acceptable excipient or carrier in addition to a hydrolysis extract of *Pulsatilla koreana* and *Anemone raddeana* and/or at least one extract selected from the group consisting of *Anthriscus sylvestris, Bupleurum longiradiatum, Crinum latifolium*, and *Adonis* amurenis.

The pharmaceutical composition may be formulated in an oral dosage form, such as a powder, granules, a tablet, a capsule, a suspension, an emulsion, a syrup, a liquid, or an aerosol, or in the form of an external preparation, a suppository, and a sterile injection solution, according to a conventional method for each form. Examples of a carrier, an excipient, and a diluent that may be contained in the pharmaceutical composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and a mineral oil. The pharmaceutical composition may be prepared by using a diluent or an excipient that is usually used, such as a filler, an extender, a binder, a humectant, a disintegrant, or a surfactant. Examples of a solid preparation for oral administration includes a tablet, pills, a powder, granules, a capsule, and the like. These solid preparations may be prepared by mixing the composition containing as an active ingredient a hydrolysis extract of *Pulsatilla koreana* and *Anemone raddeana* of the present invention with at least one excipient, for example, starch, calcium carbonate, sucrose or lactose, gelatin, or the like. Also, a lubricant, such as magnesium stearate or talc, may be used in addition to simple excipients. Examples of a liquid preparation for oral administration correspond to a suspension, a liquid for internal use, an emulsion, a syrup, and the like, and may contain simple diluents that are frequently used, such as water and liquid paraffin, as well as several excipients, such as a humectant, a sweetener, a flavoring agent, and a preservative. Examples of a preparation for parenteral administration include a sterile aqueous solution, a non-aqueous solvent, a suspension, an emulsion, a freeze-dried agent, and a suppository. Examples of the non-aqueous solvent and suspension may include propylene glycol, polyethylene glycol, vegetable oils such as olive oil, injectable esters, such as ethylolate, and the like. Examples of a material for the suppository may include Witepsol, Macrogol, Tween 61, cocoa butter, laurin butter, glycerogelatin, and the like.

The dose of the pharmaceutical composition may vary depending on the age, sex, and body weight of a subject to be treated, the particular disease or pathological condition to be treated, the severity of a disease or pathological condition, the route of administration, and the judgment of a prescriber. The determination of the dose based on these factors is within the level of a person skilled in the art, and the general dose is in the range of approximately 0.01 mg/kg/day to 2000 mg/kg/day. A more preferable dose is 0.1 mg/kg/day to 500 mg/kg/day. The administration may be conducted once a day or several times in a divided dose per day. The dose is not intended to limit the scope of the present invention in any aspect.

The pharmaceutical composition may be administered to mammals, such as rats, domestic animals, and humans, via various routes. All manners of administration may be predicted, and for example, the administration may be conducted through oral, rectal, intravenous, intramuscular, subcutaneous, endometrial, intracerebroventricular injection, and especially, the administration may be conducted on an affected area where an inflammatory disease progresses by direct injection.

The term "anti-inflammatory" encompasses the alleviation of an inflammatory disease (the reduction of a symptom) and the inhibition or delay of the development of such a disease.

The "inflammatory disease" may be defined as a pathological symptom caused by an inflammatory response characterized by an external physical or chemical stimulus, an infection from external infectious sources, such as bacteria, fungi, viruses, and various allergens, or a local or systemic biological defense response to autoimmunity, and examples of the inflammatory disease may be asthma, allergic and non-allergic rhinitis, chronic and acute rhinitis, chronic and acute gastritis or enteritis, ulcerative gastritis, acute and chronic nephritis, acute and chronic hepatitis, chronic obstructive pulmonary disease, pulmonary fibrosis, irritable bowel syndrome, inflammatory pain, migraine, headache, back pain, fibromyalgia, myofascial disease, viral infections (e.g., type C infection), bacterial infections, fungal infections, burns, wounds by surgical or dental surgery, hyper-prostaglandin E syndrome, atherosclerosis, gout, arthritis, rheumatoid arthritis, ankylosing spondylitis, Hodgkin's disease, pancreatitis, conjunctivitis, iritis, scleritis, uveitis, dermatitis (including atopic dermatitis), eczema, multiple sclerosis, and the like.

The "inflammatory disease" may be especially an inflammatory spondyloarthropathy or may be spinal stenosis, rheumatoid arthritis, lumbar disc disease, cervical disc disease, spinal stenosis, frozen shoulder, and degenerative arthritis.

In addition, the anti-inflammatory composition containing a hydrolysis extract of *Pulsatilla koreana* and *Anemone raddeana* and an angiogenesis inhibitor may be a health functional food.

The health functional food may further contain a food acceptable supplement additive in addition to the anti-inflammatory composition containing as active ingredients *Pulsatilla koreana, Anemone raddeana*, and an angiogenesis inhibitor.

The health functional food includes a form of a tablet, a capsule, pills, or a liquid preparation, and examples of a food to which the hydrolysis extract of *Pulsatilla koreana* and *Anemone raddeana* of the present invention can be added may include various types of foods, beverages, gums, teas, vitamin complexes, health functional foods, and others.

Advantageous Effects of Invention

The present invention can contribute to the development of a novel natural product drug for treatment of an inflammatory spondyloarthropathy, the drug containing a hydrolysis extract of *Pulsatilla koreana* and *Anemone raddeana* and/or an additional angiogenesis inhibitor.

MODE FOR CARRYING OUT THE INVENTION

Hereinafter, preferable exemplary embodiments of the present invention will be described in detail. However, the present invention is not limited to the exemplary embodiments described herein and can be embodied in many different forms. Rather, these exemplary embodiments are provided so that the present disclosure will be thorough and complete and will fully convey the scope of the disclosure to those skilled in the art.

Example 1: Preparation of Organic Solvent Extracts of Plants

Example 1-1: Preparation of Organic Solvent Extract of *Pulsailla koreana* (Pk-ex)

After 150 g of *Pulsatilla koreana* was collected and ground, 100 g was taken therefrom, and then 300 ml of methanol was added thereto, followed by primary reflux extraction for 5 hours. Then, the extract was filtered and the supernatant was stored, and then 300 ml of methanol was added to the residual body of the plant, followed by secondary reflux extraction for 5 hours. After filtration, the first and second methanol layers were mixed and concentrated to half the volume by distillation under reduced pressure. To this was added 200 ml of hexane, and the mixture was shaken and then left standing for 5 minutes, and the hexane layer was discarded and the methanol layer was collected and dried. To the dried product was added 30 ml of ethanol, and the mixture was stirred and then left standing, and the resulting insoluble fraction was removed by filtration and the ethanol layer was dried (Pk-ex).

Example 1-2: Preparation of Organic Solvent Extract of *Anemone raddeana* Roots (Ar-ex)

By the same method as in Example 1-1, 5.13 g of an extract of *Anemone raddeana* roots (Ar-ex) was obtained.

Example 1-3: Preparation of Extract of *Hedera colchica* Leaves (Hc-ex)

After 300 g of *Hedera colchica* leaves was ground, 200 g was taken therefrom, and then 400 ml of methanol was added thereto, followed by primary reflux extraction for 5 hours. The extract was filtered and the methanol layer was stored, and then 400 ml of methanol was again added to the residual body of the plant, followed by secondary reflux extraction for 5 hours. The methanol layers after the primary and secondary reflux were mixed, and then concentrated to about 300 ml, and thereafter 300 ml of a hexane layer was added thereto, followed by shaking, and then the hexane layer was discarded and the methanol layer was collected. By the same method as described above, degreasing was repeated twice. After the methanol layer was dried, 400 ml of ethanol was added to the dried product, shaken, and left standing at room temperature for 12 hours. The resulting insoluble fraction was removed by filtration, and the ethanol layer was dried to give 3.45 g of an extract of *Hedera colchica* leaves (Hc-ex). The chromatography analysis confirmed that HcolA-ester (hederacolchiside F) and HcolA1-ester (hederacolchiside E) were contained therein.

Example 2: Preparation of Fermentation Extract of Plant

Example 2-1: Preparation of *Pulsatilla koreana* Ferment Extract (Pk-ex)

After 150 g of *Pulsatilla koreana* was ground, 100 g was taken therefrom and placed in a fermentation bath, and 150 g of water was added and mixed, followed by secondary grinding by ultrasonication. After the secondary grinding was ended, the ground material was stirred at 37° C. for 150 minutes, and then the reaction product was heated at 80° C. for 30 minutes. The resulting material was cooled to room temperature and then concentrated to half of the total volume, and thereafter 400 ml of methanol was added thereto, followed by stirring at room temperature for 5 hours. The methanol soluble fraction was filtered and stored, and 400 ml of methanol was again added to the residual body of the plant, stirred for 5 hours, and then filtered. The methanol solution was mixed with the previous one. The methanol soluble fraction obtained by mixing was concentrated under reduced pressure and then dried. To the dried material was added 50 ml of ethanol, followed by mixing. The mixture was left standing at room temperature for 2 hours, and then the resulting insoluble fraction was removed by centrifugation or filtration. The ethanol soluble fraction was dried to give 9.7 g of solids.

Hederacolchiside A therein was quantified. The quantification of hederacolchiside A and hederacolchiside A1 was conducted by the method of Y. Zhao et al. HPLC (Lab Alliance Series III, SSI, USA) with C18 analytic column (250 mm×4.5 cm, Alltech Associates Co. USA) using acetonitrile (A) and 0.1% phosphoric acid aqueous solution (B) concentration gradient solvent system (moving speed: 1.0 ml/min, measured at 203 nm). The standard curve was created by purchasing hederacolchiside A and hederacolchiside A1 (CoreSciences, info@coresciences.co.kr) as standard reagents, and extracts were fractionated by HPLC, and then the intensities of peaks of hederacolchiside A and A1 were measured and quantified by insertion into the standard curve. As a result of quantification, HcolA was 103.4 mg in 9.7 g produced, indicating a HcolA yield of 1.07%. The concentrate (Pf-ex) of 9.7 g was dissolved in physiological saline and made into a preparation with a HcolA concentration of 1.0 mg/ml.

Example 2-2: Preparation of Fermentation Extract of *Anemone raddeana* Roots (Af-ex)

*Anemone raddeana* roots were processed by the same method as in Example 2-1 to give 11.3 g of a concentrate, in which HcolA1 was 180.5 mg, indicating an HcolA1 yield of 1.87%. The concentrate (Af-ex) was dissolved in physiological saline to an HcolA1 concentration of 1.0 mg/ml, and utilized as a preparation.

Example 3: Preparation of Organic Solvent Extract of Mixture Fermentation Product Example 3-1: Preparation of PfAr-ex, Organic Solvent Extract of Fermentation Product of Mixture of *Pusailla koreana* and *Anemone raddeana* Roots After 150 g of *Pulsatilla koreana* was finely ground, 100 g was taken therefrom and placed in a water tank, and 4.13 g of an extract of *Anemone raddeana* roots (Ar-ex) was added, and 150 ml of water was added, followed by ultrasonication for 5 minutes and reaction with stirring at 37° C. for 3 hours. Upon completion of the reaction, the temperature was raised to 80° C., followed by heating for 20 minutes. When the temperature of the fermentation product was room temperature, 400 ml of methanol was added thereto, followed by primary stirring at room temperature for 6 hours. After stirring and filtration, the methanol extract was stored, and 400 ml of methanol was again added to the residual body of the plant, followed by secondary stirring for 6 hours and then filtration, and the primary and secondary methanol extracts were mixed and concentrated to about 300 ml under reduced pressure.

To this was added 300 ml of hexane, followed by shaking for 15 minutes, and then the hexane layer was removed, and 300 ml of hexane was again added to the methanol layer, followed by shaking, and then the hexane layer was removed. The methanol layer was collected and dried under reduced pressure to give 5.43 g of an extract (PfAr-ex). The chromatography analysis confirmed that 98.3 mg (1.81%) of HcolA and 145.5 mg (2.68%) of HcolA1 were contained in 5.43 g of PfAr-ex.

Example 3-2: Preparation of AfPk-ex, Organic Solvent Extract of Fermentation Product of *Anemone raddeana* Root Mixed with *Pulsatilla koreana* Extract (Pk-ex)

By the same method as in Example 3-1, the *Pulsatilla koreana* extract (Pk-ex) was added to *Anemone raddeana* roots, followed by fermentation and then solvent extraction, thereby obtaining 4.6 g of an extract (AfPk-ex). The chromatography analysis confirmed that 108.3 mg of HcolA and 123.28 mg of HcolA1 were contained in 4.6 g of the extract (AfPk-ex). The extract was dissolved in physiological saline to be made into a preparation of HcolA 1.0 mg+HcolA1 1.1 mg/ml.

The mixing ratio of HcolA and HcolA1 in PfAr-ex or and AfPk-ex obtained in Examples 2-1 and 2-2 was investigated. As for the preparation of extracts of *Pulsatilla koreana* and *Anemone raddeana* containing high concentrations of HcolA and HcolA1, the contents per g of the extracts, respectively, obtained from *Pulsatilla koreana* and *Anemone raddeana* were HcolA 10.6 mg/g ex (HcolA 103.4 mg/9.7 g) and HcolA1 18.6 mg/g ex (HcolA1 180.5 mg/9.7 g). However, the contents per g of the extracts PfAr-ex and AfPk-ex obtained by cross hydrolysis through mixed fermentation of *Pulsatilla koreana* and *Anemone raddeana* were HcolA 23.5/g-ex and HcolA1 26.8 mg/g-ex, which were higher contents than fermentation each (Table 1).

TABLE 1

| Classification | Hederacolchiside contents (mg/g) according to hydrolysis | |
|---|---|---|
| | Extraction each | Cross hydrolysis |
| *Pulsatilla koreana* | Hederacolchiside A 10.6 | Hederacolchiside A 23.5 |
| *Anemone raddeana* | Hederacolchiside A1 18.6 | Hederacolchiside A1 26.8 |

As for PfAr-ex as an example, most substances other than saponins were removed during solvent extraction of *Anemone raddeana* roots, and thus an extract (Ar-ex) with a high HcolF content was obtained. The fermentation of this extract having a high content of HcolF mixed with *Anemone raddeana* roots as fermentation substrate increased the rate of hydrolysis, leading to complete hydrolysis.

Example 4: Formulation of Preparation Containing High Concentrations of Saponins Including HcolA and HcolA1

Daiion HP20 with water was poured into a column with a diameter of 2 cm to form a solid with a height of 40 cm, and 500 ml of distilled water was allowed to pass through the column to stabilize the column. Then, 100 mg of AfPk-ex dissolved in 10 ml of water was evenly applied and adsorbed to the column. Thereafter, the column was washed two times with 5 ml of water each time, and then 200 ml of water was added to pass through the column for 30 minutes. Then, 200 ml of a 20% methanol solution was slowly passed through the column, and subsequently a 30% methanol aqueous solution was passed through the column. The eluate was collected in 10 ml each in a test tube simultaneously with the start of the passage of 20% methanol, and the start and end of the outflow of saponins were checked by color responses of saponins. The saponin response was observed in the 35th to 41st test tubes, from which 22.2 mg of a preparation containing high concentrations of saponins containing HcolA and HcolA1 was obtained by drying.

As for the color responses of saponins, the eluate was taken out from each test tube by using a capillary tube, dripped on a silica gel plate, and dried, and then acetic anhydride was sprayed thereon; followed by heating at 110° C. The start and end of saponin elution was determined by the appearance of red spots.

Example 5: Preparation of Plant Extract Having Angiogenesis Inhibitory Action In the present invention, an anti-inflammatory effect can be enhanced by mixing an angiogenesis inhibitory plant extract with an extract containing high concentrations of saponins having hederagenin and oleanolic acid as aglycones.

Example 5-1: Preparation of Extract of *Adonis amurensis*

*Adonis amurensis* is a plant containing angiogenesis inhibitors, such as cymarin, cymarilic acid, and cymarol. Dried roots of *Adonis amurensis* were ground, and 200 g was mixed with 500 ml of methanol, stirred for 12 hours, and then filtered. Thereafter, the methanol layer was separately stored, and 300 ml of methanol was again added to the residual body of the plant and stirred for 7 hours, to again give a methanol layer. This procedure was further repeated once. The methanol layer was collected and dried in a distillation machine under reduced pressure, and 100 ml of methanol was added thereto, followed by shaking, and then the mixture was left standing and the resulting insoluble fraction was removed by filtration. To the methanol layer was added 100 ml of hexane, followed by shaking, and then the hexane layer was discarded. The above-described hexane treatment procedure was further repeated once. The remaining methanol layer was dried, and then dissolved in 50 ml of water added thereto, and 100 ml of ethyl acetate was added thereto, and the mixture was shaken for 10 minutes and left standing, and then the ethyl acetate layer was separated and stored. To the water layer was again added 50 ml of ethyl acetate, and the mixture was shaken and left standing, and then the ethyl acetate layer was separated and mixed with the previous ethyl acetate. Then the ethyl acetate layer was dried, and 40 ml of ethyl acetate was added to dissolve solids, and 10 ml of hexane was added thereto, followed by mixing through shaking. The mixture was left standing in a refrigerator for 12 hours, and then the resulting insoluble fraction (containing toxic cardenolides) was removed by filtration, and the ethyl acetate/hexane solution was dried, and again washed with ethanol, and dried to give 2.9 g of a dried material, expressed as Ad-ex.

It was confirmed by the method of Y J You et al. that 2.9 g of AD-ex contained 90 mg of a cymarin/cymarilic acid/cymarol (CCC) mixture, and this mixture was dissolved in ethanol to have 1000 μg CCC/100 ml=10 μg CCC/ml.

Example 5-2: Preparation of *Bupleurum longiradiatum* Extract

*Bupleurum longiradiatum* contains the angiogenesis inhibitor bupleurotoxin and acetylbupleurotoxin (BTPa). The entire plant of *Bupleurum longiradiatum* dried in shade was ground, and 100 g was taken therefrom, and 400 ml of methanol was added thereto, and the mixture was stirred under nitrogen for 5 hours. The resulting material was filtered, and then methanol was stored under nitrogen gas, and the same amount of methanol was added to the residual body of the plant, followed by stirring under nitrogen gas for 5 hours. The mixture was filtered, and then the methanol layer was mixed with the previous methanol, and distilled under reduced pressure in the presence of nitrogen, and concentrated to ⅓ of the total solution. To this was added 200 ml of ethyl acetate, followed by shaking, and then the ethyl acetate layer was taken and dried. To this was added 5 ml of anhydrous ethyl alcohol, and the precipitate generated was removed by centrifugation, thereby giving an extract of *Bupleurum longiradiatum* (BPT-ex). The extract contained 0.3 mg of bupleurotoxin/acetylbupleurotoxin.

Example 5-3: Preparation of *Crinum latifolium* Extract

*Crinum latifolium* contained the angiogenesis inhibitor 2-senecioyloxy-methyl-3,4-dimethoxycoumarin (SDC). After 300 g of dried *Crinum latifolium* was finely ground, 200 g of the ground material was mixed with 400 ml of a 50% methanol aqueous solution (V/V), followed by reflux for one hour. After the reaction, the reaction product was filtered and the methanol layer was stored, and 400 ml of 50% methanol was added to the residual body of the plant and stirred at room temperature for 10 hours. Thereafter, all the methanol layers were mixed and concentrated under reduced pressure to a total amount of 100 ml. Then, 0.1 N HCl was added to the concentrate to adjust the pH to 4.5, and then 200 ml of chloroform was added, followed by shaking for 10 minutes. The chloroform layer was separated and stored, and the aqueous layer was extracted again with the same amount of chloroform. The chloroform layers were mixed and washed twice with 200 ml of water, and then dried under reduced pressure to give 2.1 g of an extract of *Crinum latifolium* (Cla-ex). 2.1 g of Cla-ex contained 8 mg of 2-senecioyloxymethyl-3,4-dimethoxycoumarin (SDC).

Example 5-4: Preparation of Deoxypodophyllotoxin (DPT) Stock Solution

Deoxypodophyllotoxin (DPT), an angiogenesis inhibitor of *Anthriscus sylvestris*, was commercially available and thus purchased for use. A DPT stock solution at 1.5 μg/ml was used by dissolving 0.15 mg of DPT in 100 ml of ethanol.

Example 5-5: Preparation of Extract of *Glycyrrhiza uralensis*

After 50 g of *Glycyrrhiza uralensis* dried in the shade was collected and ground, 10 g was taken therefrom. To this was added 40 ml of methanol, followed by reflux for one hour with stirring. The reaction product was filtered, and 40 ml of methanol was added to the residual body of the plant, followed by reflux for one hour. After filtration, the methanol soluble fraction was mixed with the previous one, and then the mixture was dried after the removal of methanol.

To the dried material was added 10 ml of ethanol, followed by mixing, and the mixture was left standing at room temperature for 1 hour, and then the resulting insoluble fraction was removed. The ethanol solution was dried. To this was added 10 ml of physiological saline, followed by stirring, and then the mixture was left standing at room temperature for 12 hours and filtered, and the obtained solution was used as a preparation (Gly-ex, a crude extract of *Glycyrrhiza uralensis*). Isoliquiritin in the *Glycyrrhiza uralensis* extract was quantified after the standard curve was prepared using HPLC using an isoliquiritin standard product. For HPLC, a C-18 (reverse-phase) column was used, and gradient elution was conducted using solvents (water/formic acid (100/0.04) and acetonitrile). The elution rate was 0.2 m/mi, and the elution temperature was room temperature. The detection was conducted at a wavelength of 368 nm. In the 1 ml of the obtained crude extract of *Glycyrrhiza uralensis,* 4.1 mg of isoliquiritin was contained.

Example 6: Anti-Inflammatory Effects of Anti-Inflammatory Compositions Containing Hydrolysis Extracts of *Pulsatilla koreana* and *Anemone raddeana*

Anti-inflammatory compositions were prepared using the hydrolysis extracts prepared in Examples 1 to 5 as shown in Table 2 below, and the anti-inflammatory effects thereof were examined on rats with edema induced with canrageenan.

TABLE 2

| Composition | Composition |
|---|---|
| Control | physiological saline, 2 ml |
| Preparation 1 | Pf-ex(1 ml) |
| Preparation 2 | Pf-ex(1 ml) + DPT(1 ml) |
| Preparation 3 | Af-ex(1 ml) |
| Preparation 4 | Af-ex(1 ml) + DPT(1 ml) |
| Preparation 5 | Pf-ex(1 ml) + Af-ex(1 ml) |
| Preparation 6 | Pf-ex(1 ml) + Af-ex(1 ml) + DPT(1 ml) |
| Preparation 7 | Pf-ex(1 ml) + Af-ex(1 ml) + Gly-ex(1 ml) |
| Preparation 8 | Pf-ex(1 ml) + Af-ex(1 ml) + Ad-ex(1 ml) |
| Preparation 9 | AfPk-ex(1 ml) |
| Preparation 10 | AfPk-ex(1 ml) + DPT(1 ml) |
| Preparation 11 | AfPk-ex(1 ml) + Gly-ex(1 ml) |
| Preparation 12 | PfAr-ex(1 ml) |
| Preparation 13 | PfAr-ex(1 ml) + Gly-ex(1 ml) |
| Preparation 14 | Pf-ex(1 ml) + Af-ex(1 ml) + Gly-ex(1 ml) + DPT (1 ml) |
| Preparation 15 | AfPk-ex(1 ml) + DPT(1 ml) + Gly-ex(1 ml) |
| Comparative Example 1 | Indomethacin 10 mg/kg, oral administration |
| Comparative Example 2 | HcolA 1 mg + HcolA1 1 mg |
| Comparative Example 3 | Pk-ex(1 ml) |
| Comparative Example 4 | Ar-ex(1 ml) |
| Comparative Example 5 | Hc-ex(1 ml) |
| Comparative Example 6 | Direct injection of Preparation 14 into point of carrageenan injection |

Each experimental group was composed of three Wistar rats, and the edema was formed by subplantar injection of 0.1 ml of a 1% (w/v) lambda carrageenan solution to the left hind paw of the rats. By the same method, 0.1 ml of physiological saline was injected into the right hind paw. A control, Preparations 1 to 16, and comparative examples 1 to 5 were intraperitoneally injected into the rats at an amount of 1 ml per animal one hour before edema induction, and indomethacin was orally administered one hour before edema induction. For the control, 2 ml of physiological saline was used. As for Comparative Example 1, the group was orally administered with 10 mg/kg indomethacin. The medicinal effect was assayed as percentage (%) by measuring the volume of edema from 2 hours to 4 hours in 1 hour units after carrageenan administration. [{1−S/C}×100] (S: edema volume in the preparation administration group, C: edema volume in the carrageenan administration group) The volume of edema was measured by water plethysmography. As for Preparation 16, the anti-inflammatory effect was observed by direct injection of Preparation 9 into the point of carrageenan injection on the rats. This method was used considering that in the vertebral skeletal diseases, drugs are often directly injected into affected areas in clinical practice, and the method can also be applied to the herbal acupuncture in oriental medicine. In the present invention, 0.2 ml of Preparation 14 was selected and directly injected twice at an interval of 30 minutes to the point of carrageenan injection on the left hind paw of the rats (Comparative Example 6). That is, the injection was conducted at 150 minutes and 180 minutes after carrageenan injection, and the anti-inflammatory assay was conducted 240 minutes (4 hours after carrageenan injection). Comparative Example 2 was a Preparation of 1 mg of HcolA1 mixed with 1 mg of HcolA. The control was used for a physiological saline administration group.

Preparation 1 and Preparation 3 were produced by adding physiological saline to 1 ml of Pf-ex (containing 1 mg of HcolA) and 1 ml of Af-ex (containing 1 mg of HcolA1), obtained by fermentation and solvent extraction of *Pulsatilla koreana* and *Anemone raddeana* roots, to a volume of 5 ml, and these preparations were the basis for anti-inflammatory assay of the preparations of the present invention. Preparation 1 was contrasted to preparation 3. For Preparation 3, 1 ml of Af-ex containing 1 mg of HcolA1 was collected and physiological saline was added to a total solution volume of 5 ml. Both the preparations had weak anti-inflammatory action and were even weaker than indomethacin (63.3%) of Comparative Example 1, but showed excellent anti-inflammatory action compared with Comparative Example 3 (Pk-ex, reduced edema by 23.0%), Comparative Example 4 (Ar-ex, reduced edema by 19.4%), Comparative Example 5 (Hc-ex, reduced edema by 15.5%).

Preparation 2 was obtained by adding 1.5 μg of deoxypodophyllotoxin (DPT), an angiogenesis inhibitor, to Preparation 1 of *Pulsatilla koreana*. Preparation 2 showed enhanced anti-inflammatory activity by 7.0% compared with Preparation 1. This was due to a synergistic effect in the anti-inflammatory action through angiogenesis inhibition of DPT.

Preparation 4 was obtained by adding DPT to Preparation 3 and showed enhanced anti-inflammatory activity. This was due to the synergistic effect of DPT. Preparation 4 showed no significant difference compared with Preparation 2.

Preparation 5 was obtained by mixing Preparation 1 and Preparation 3 at 1:1. The activity of Preparation 5 was 60.5%, significantly higher than that of Preparation 1 or Preparation 3. Pf-ex and Af-ex of Preparation 5 contained 1.0 mg of HcolA and 1.0 mg of HcolA1, respectively. The amount of the action components was calculated as (HcolA 1.0 mg+HcolA1 1.0 mg)/5 ml. The amount of action substances in Preparation 5 was twice as large as that in Preparation 1 or Preparation 3. The enhancement of anti-inflammatory action of Preparation 5 was due to a quantitative increase in action substances.

Preparation 5 was contrasted to Comparative Example 2. For Comparative Example 2, pure action substances were used to prepare (HcolA 1 mg+HcolA1 1 mg)/5 ml, of which the anti-inflammatory activity (40.7%) was much lower than that of Preparation 5. Consequently, the high activity of Preparation 5 was construed as being due to the presence of other substances that enhance the anti-inflammatory effect, in addition to HcolA or HcolA1 in the extract.

Preparation 6 was obtained by adding DPT to Preparation 5 and showed enhanced anti-inflammatory action by 9.2%.

Preparation 7 was obtained by adding Gly-ex, a *Glycyrrhiza uralensis* extract, instead of DPT in Preparation 6. Preparation 7 and Preparation 6 showed no significant difference in the anti-inflammatory activity.

Preparation 8 was contrasted to Preparations 6 and 7 and obtained by adding, as an angiogenesis inhibitor, an *Adonis amurensis* extract (Ad-ex) instead of DPT or Gly-ex. Among these three angiogenesis inhibitors, the *Adonis amurensis* extract (Ad-ex) showed the strongest anti-inflammatory synergistic effect.

Preparation 9 was obtained by adding a *Pulsatilla koreana* solvent extract (Pk-ex) to *Anemone raddeana* roots and fermenting the mixture, and showed a similar composition and effect to Preparation 5.

Preparation 10 was obtained by adding DPT to Preparation 9 and showed an anti-inflammatory action as high as 63.3%, and the synergistic effect by the addition of DPT was 7.3%.

Preparation 11 was obtained by adding a *Glycyrrhiza uralensis* extract (Gly-ex) to Preparation 9 and showed a very high anti-inflammatory effect of 72.4%. The anti-inflammatory action synergistic effect by the addition of Gly-ex was 13.7%.

Preparation 12 was obtained by adding a solvent extract of *Anemone raddeana* roots (Ar-ex) to *Pulsatilla koreana* and conducting fermentation and showed a similar composition and effect to Preparation 9.

Preparation 13 was obtained by adding a *Glycyrrhiza uralensis* extract (Gly-ex) to PfAr-ex, which was an extract obtained by adding a solvent extract of *Anemone raddeana* roots (Ar-ex) to *Pulsatilla koreana* and conducting fermentation, and had a similar anti-inflammatory action to Preparation 11.

Preparation 14 was obtained by adding the angiogenesis inhibitors DPT and Gly-ex to Preparation 5 and showed an anti-inflammatory action enhanced by 18.6%, compared with 60.5% of Preparation 5.

Preparation 15 was obtained by adding DPT and Gly-ex to Preparation 9 and showed a similar anti-inflammatory action to Preparation 14.

As for Comparative Example 6, the volume of the rat hind paw was reduced by 87% one hour after the direct injection of Preparation 14 was completed. In three rats for Comparative Example 3, the left hind paw showed no significant difference in edema volume compared with the right paw without carrageenan injection, and their movements were also free. It was therefore considered that the *Adonis amurensis* extract showed no special signs of toxicity on rats and thus the direct injection of Preparation 9 or the like into an affected area would enhance an anti-inflammatory effect as shown in Comparative Example 6.

The experimental results are shown in Table 3. The edema size reduction percent (%) was expressed as the ratio of the edema size by each preparation after each hour relative to the size of edema (control) by carrageenan injection after each hour as shown below, and the average reduction percent of edema was expressed as an average value of the reduction percent values of each preparation after 2, 3, or 4 hours.

Edema size reduction percent (%)={1−(edema size by each preparation/edema size by control)}×100

TABLE 3

| Composition | Edema size over time (hour) after treatment (reduction percent, %) | | | Average edema reduction percent (%) |
|---|---|---|---|---|
| | 2 hours | 3 hours | 4 hours | |
| Control | 0.814 ± 0.045 | 0.831 ± 0.011 | 0.867 ± 0.064 | (0) |
| Preparation 1 | 0.400 ± 0.088(51) | 0.467 ± 0.019(44) | 0.428 ± 0.056(51) | (48.6) |
| Preparation 2 | 0.357 ± 0.013(56) | 0.363 ± 0.045(56) | 0.387 ± 0.082(55) | (55.6) |
| Preparation 3 | 0.443 ± 0.022(45) | 0.450 ± 0.056(45) | 0.513 ± 0.01(41) | (36.6) |
| Preparation 4 | 0.398 ± 0.078(51) | 0.369 ± 0.035(55) | 0.401 ± 0.073(53) | (53.0) |
| Preparation 5 | 0.304 ± 0.012(63) | 0.340 ± 0.043(59) | 0.351 ± 0.023(59.5) | (60.5) |
| Preparation 6 | 0.287 ± 0.057(65) | 0.252 ± 0.087(69.7) | 0.221 ± 0.036(74.5) | (69.7) |
| Preparation 7 | 0.309 ± 0.034(62) | 0.286 ± 0.031(65.8) | 0.208 ± 0.065(76) | (67.9) |
| Preparation 8 | 0.201 ± 0.021(75) | 0.187 ± 0.078(77) | 0.189 ± 0.037(78) | (76.6) |
| Preparation 9 | 0.354 ± 0.012(56.5) | 0.342 ± 0.043(58.8) | 0.331 ± 0.023(61.8) | (58.7) |
| Preparation 10 | 0.304 ± 0.044(63) | 0.300 ± 0.083(64) | 0.321 ± 0.046(63) | (63.3) |
| Preparation 11 | 0.229 ± 0.056(72) | 0.228 ± 0.045(73) | 0.237 ± 0.098(73) | (72.4) |
| Preparation 12 | 0.296 ± 0.074(64) | 0.341 ± 0.059(59) | 0.357 ± 0.078(59) | (60.0) |
| Preparation 13 | 0.214 ± 0.055(74) | 0.214 ± 0.055(74) | 0.218 ± 0.085(75) | (73.2) |
| Preparation 14 | 0.174 ± 0.033(79) | 0.182 ± 0.025(78) | 0.182 ± 0.046(79) | (78.6) |
| Preparation 15 | 0.214 ± 0.055(74) | 0.211 ± 0.056(74.6) | 0.218 ± 0.085(75) | (74.5) |
| Comparative Example 1 | 0.304 ± 0.012(63) | 0.300 ± 0.043(64) | 0.321 ± 0.023(63) | (63.3) |
| Comparative Example 2 | 0.456 ± 0.069(44) | 0.508 ± 0.059(39) | 0.527 ± 0.034(39) | (40.7) |
| Comparative Example 3 | 0.632 ± 0.059(22) | 0.639 ± 0.077(23) | 0.652 ± 0.048(25) | (23..0) |
| Comparative Example 4 | 0.663 ± 0.038(19) | 0.679 ± 0.045(18) | 0.681 ± 0.063(21) | (19.4) |
| Comparative Example 5 | 0.674 ± 0.066(17) | 0.712 ± 0.053(14) | 0.736 ± 0.053(15) | (15.5) |
| Comparative Example 6 | — | — | 0.165 ± 0.032(79.7) | (79.7) |

To sum up the relationships between the preparations of the present invention and anti-inflammatory action, Pf-ex (Preparation 1) or Af-ex (Preparation 3) showed an enhanced anti-inflammatory action compared with the single plant preparation Pk-ex (Comparative Example 3) or Ar-ex (Comparative Example 4), and as for an additional verification experiment for Preparation 5 obtained by mixing these two extracts, the experimental results confirmed that that Preparation 5 obtained by mixing Pf-ex (0.5 ml) and Af-ex (0.5 ml) showed an edema reduction percent of 55.2%, the mixed use of Pf-ex and Af-ex resulted in a synergistic effect with respect to anti-inflammatory action. However, the group administered with Comparative Example 2 prepared by isolating pure action substances in Preparation 5 showed weak anti-inflammatory action. Ultimately, it was considered that action-enhancing substances other than the pure action substances were contained in Preparation 5, and the addition of the angiogenesis inhibitors DPT, Gly-ex, Ad-ex, and the like to Preparation 5 significantly enhanced anti-inflammatory action.

Preparation 14 and Preparation 15 obtained by adding DPT and Gly-ex to Preparation 5 and Preparation 9 showed the strongest anti-inflammatory action among the preparations of the present invention.

Preparation Example 1. Pharmaceutical Preparations

A composition for prevention or treatment of an anti-inflammatory disease, the composition containing, as active ingredients, a hydrolysis extract of *Pulsatilla koreana* and *Anemone raddeana* or a cross hydrolysis extract thereof, and an angiogenesis inhibitory extract may be prepared as an oral preparation or an injection preparation. Especially, the injection preparation can enhance an anti-inflammatory effect by direct injection into an affected area.

Preparation Example 1-1: Preparation of Powder

A powder was prepared by mixing 2 g of a mixture of the hydrolysis extract of *Pulsatilla koreana* and *Anemone raddeana* or the cross hydrolysis extract thereof and the extract of *Adonis amurensis* of the present invention with 1 g of lactose and filling the resulting mixture in an airtight bag to prepare a powder.

Preparation Example 1-2: Preparation of Tablet

A tablet was prepared by mixing 100 mg of a mixture of the hydrolysis extract of *Pulsatilla koreana* and *Anemone raddeana* or the cross hydrolysis extract thereof and the extract of *Glycyrrhiza uralensis* of the present invention, 100 mg of microcrystalline cellulose, 60 mg of lactose hydrate, 20 mg of low-substituted hydroxypropyl cellulose, and 2 mg of magnesium stearate and tableting the resulting mixture according to a typical tablet formulation method.

Preparation Example 1-3: Preparation of Capsule

A capsule was prepared by mixing 100 mg of a mixture of the hydrolysis extract of *Pulsatilla koreana* and *Anemone raddeana* or the cross hydrolysis extract thereof and the extract of *Adonis amurensis* of the present invention, 100 mg of microcrystalline cellulose, 60 mg of lactose hydrate, 20 mg of low-substituted hydroxypropyl cellulose, and 2 mg of magnesium stearate and filling the resulting mixture in a gelatin capsule.

Preparation Example 1-4: Preparation of Injection

An injection was prepared by mixing 10 mg of a mixture of the hydrolysis extract of *Pulsatilla koreana* and *Anemone raddeana* or the cross hydrolysis extract thereof and the extract of *Glycyrrhiza uralensis* of the present invention, an appropriate amount of injectable sterile distilled water, and an appropriate amount of a pH adjuster and then allowing the above ingredients to be contained per ampoule (2 ml) according to a typical injection formulation method.

The invention claimed is:

1. A method for treating an inflammatory disease in a subject in need thereof, comprising administering to the subject an effective amount of a composition comprising a water-hydrolysis fermentation product of a ground material of *Anemone raddeana, Pulsatilla chinensis*, or *Pulsatilla cernua;* optionally, an organic solvent extract of *Pulsatilla koreana*; and at least one angiogenesis inhibitor selected from the group consisting of organic solvent extract of *Adonis amurensis, Glycyrrhiza uralensis* and deoxypodophyllotoxin (DPT).

2. The method of claim 1, wherein the organic solvent extract contained in the composition is obtained by extraction with at least one solvent selected from the group consisting of C1 to C4 lower alcohols, acetone, and ethyl acetate.

3. The method of claim 1, wherein the composition comprises an extract obtained by mixing and hydrolyzing a water-hydrolysis fermentation product of a ground material of *Anemone raddeana, Pulsatilla chinensis*, or *Pulsatilla cernua* and an extract of *Pulsatilla koreana*, with an organic solvent selected from C1 to C4 lower alcohols, acetone, and ethyl acetate.

4. The method of claim 1, wherein the inflammatory disease is at least one selected from the group consisting of spinal stenosis, rheumatoid arthritis, lumbar disc disease, cervical disc disease, spinal stenosis, frozen shoulder, and degenerative arthritis.

5. The method of claim 2, wherein the inflammatory disease is at least one selected from the group consisting of spinal stenosis, rheumatoid arthritis, lumbar disc disease, cervical disc disease, spinal stenosis, frozen shoulder, and degenerative arthritis.

6. The method of claim 3, wherein the inflammatory disease is at least one selected from the group consisting of spinal stenosis, rheumatoid arthritis, lumbar disc disease, cervical disc disease, spinal stenosis, frozen shoulder, and degenerative arthritis.

* * * * *